US012077735B2

United States Patent
Lewis et al.

(10) Patent No.: US 12,077,735 B2
(45) Date of Patent: Sep. 3, 2024

(54) METHOD OF STILLAGE CLARIFICATION USING TRANSGLUTAMINASE

(71) Applicant: POET Research, Inc., Sioux Falls, SD (US)

(72) Inventors: Stephen M. Lewis, Sioux Falls, SD (US); Tad Scott Hepner, Hartford, SD (US)

(*) Notice: Subject to any disclaimer, the term of this patent is extended or adjusted under 35 U.S.C. 154(b) by 440 days.

(21) Appl. No.: 17/071,794

(22) Filed: Oct. 15, 2020

(65) Prior Publication Data

US 2021/0108163 A1 Apr. 15, 2021

Related U.S. Application Data

(60) Provisional application No. 62/915,242, filed on Oct. 15, 2019.

(51) Int. Cl.
*C12C 12/00* (2006.01)
*C12N 1/16* (2006.01)
*C12P 7/06* (2006.01)

(52) U.S. Cl.
CPC .............. *C12C 12/006* (2013.01); *C12N 1/16* (2013.01); *C12P 7/06* (2013.01); *C12Y 203/02013* (2013.01)

(58) Field of Classification Search
CPC ...... C12C 12/006; C12N 1/16; C12N 9/1044; C12P 21/00; C12P 7/06; C12Y 203/02013
See application file for complete search history.

(56) References Cited

U.S. PATENT DOCUMENTS

2007/0037267 A1* 2/2007 Lewis .................. C12P 7/06
435/161

FOREIGN PATENT DOCUMENTS

CA          2782128 A1 *  6/2011  ........... C12N 9/2428

OTHER PUBLICATIONS

Buchert et al. (2010) "Crosslinking Food Proteins for Improved Functionality" Annu Rev Food Sci Technol 1:113-138.
Cheng et al. (2017) "Optimization of Protein Removal from Soybean Whey Wastewater Using Chitosan Ultrafiltration" Journal of Food Process Engineering 40(e12370):1-9.
Cui et al. (2016) "Cell Spreading and Viability on Zein Films may be Facilitated by Transglutaminase" Colloids and Surfaces B: Biointerfaces 145:839-844.
Fatima and Khare (2018) "Recent advances in the application of microbial transglutaminase crosslinking in cheese and ice cream products: A review" Microbiological Research 215:7-14.
Gaspar et al. (2015) "Action of microbial transglutaminase (MTGase) in the modification of food proteins: A review" Food Chemistry 171:315-322.

(Continued)

*Primary Examiner* — Latosha Hines
(74) *Attorney, Agent, or Firm* — FisherBroyles, LLP; Cara L. Crowley-Weber; Cary Reeves

(57) ABSTRACT

Methods, compositions, and systems for fermentation, particularly large scale operations for production of ethanol and dried distiller's grain are provided. Addition of a transglutaminase source to a process stream aids in removing protein from the system in order to provide a high protein feed product and/or provide clarified backset for fermentation. Transglutaminase can be in reagent form or can be produced by microorganisms added to the process stream.

24 Claims, 4 Drawing Sheets

(56) References Cited

OTHER PUBLICATIONS

Gharibzahedi and Chronakis (2018) "Crosslinking of milk proteins by microbial transglutaminase: Utilization in functional yogurt products" Food Chemistry 245:620-632.

Gharibzahedi et al. (2018) "Recent advances in the application of microbial transglutaminase crosslinking in cheese and ice cream products: A review" International Journal of Biological Macromolecules 107:2364-2374.

Griffin et al. (2002) "Transglutaminases; Nature's Biological Glues" Biochem J. 368:377-396.

Hamada and Swanson (2009) "Deamidation of Food Proteins to Improve Functionality" Critical Reviews in Food Science and Nutrition 34(3):283-292.

Kamiya (2003) "Site-Specific Cross-Linking of Functional Proteins by Transglutamination" Enzyme and Microbial Technology 33:492-496.

Kuraishi et al. (2001) "Transglutimase: Its Utilization in the Food Industry" Food Reviews International 17(2):221-246.

Martins et al. (2014) "Transglutaminases: Recent Achievements and New Sources" Appl Microbiol Biotechnol 98:6957-6964.

Moron (2008) "Toward the Assessment of Food Toxicity for Celiac Patients: Characterization of Monoclonal Antibodies to a Main Immunogenic Gluten Peptide" PlusONE 3(5):E2294 p. 1-13.

Oh (2004) "Characteristics of edible films made from dairy proteins and zein hydrolysate cross-linked with transglutaminase" International Journal of Food Science and Technology 39:287-294.

Santhi et al. (2017) "Application of Microbial Transglutiminase in Meat Foods: A Review" Critical Reviews in Food Science and Nutrition 57(10):2071-2076.

Soares (2003) "Purification and Properties of a Transglutaminase Produced by a Bacillus Circulans Strain Isolated from the Amazon Environment" Biotechnol Appl Biochem 37:295-299.

Yokoyama et al. (2004) "Properties and applications of microbial transglutaminase" Appl Microbiol Biotechnol 64:447-454.

Zhu and Tramper (2008) "Novel applications for microbial transglutaminase beyond food processing" Trends in Biotechnology 26(10):559-565.

* cited by examiner

METHOD OF STILLAGE CLARIFICATION USING TRANSGLUTAMINASE

RELATED APPLICATIONS

This application claims priority under 35 U.S.C. 119 (e) to U.S. Provisional Patent Application Ser. No. 62/915,242, entitled "Method of Improved Stillage Clarification Using Transglutaminase," filed Oct. 15, 2019 the disclosure of which is hereby incorporated by reference in its entirety.

TECHNICAL FIELD

Provided herein are methods, compositions, and systems for stillage clarification and/or protein recovery, particularly in large scale operations from production of ethanol and dried distiller's grain.

BACKGROUND OF THE INVENTION

Ethanol is a grain alcohol that is commonly used as a fuel source and can be produced from corn or other grain feedstock through the fermentation of starch. Starches are released from the processed grain, converted to sugars and then to alcohol by the addition of yeast. The alcohol is recovered using distillation. On a large scale, ethanol production requires many pieces of equipment to separate solids and liquids into the various by-products of grain fermentation.

SUMMARY OF THE INVENTION

Provided herein are compositions, systems, and methods comprising transglutaminase in fermentation or post-fermentation streams such as beer or stillage.

Provided herein are compositions comprising: a feedstock, a transglutaminase source, a microorganism, and water. In some aspects, the transglutaminase source is a microorganism that expresses transglutaminase. In some aspects, the transglutaminase source is in reagent form.

Provided herein are methods of decreasing stillage protein levels. The methods comprise adding a transglutaminase source to a fermentation reactor or to post-fermentation stillage and isolating the protein.

Provided herein are methods of isolating protein from post-fermentation stillage. The methods comprise adding a transglutaminase source to a fermentation reactor or to post-fermentation stillage and isolating the protein.

Provided herein are methods for producing a fermentation product. In some aspects, the methods comprise the following steps, not necessarily in the order listed: grinding grain to provide ground grain; combining the ground grain with water to form a slurry; providing the slurry to a fermenter; inoculating the slurry with an ethanologen, filling the fermenter to provide a fermentation broth; fermenting the slurry to form a beer containing a fermentation product; separating the fermentation product from the beer; adding transglutaminase to at least one process stream selected from the slurry, the fermentation broth, the beer, or a process stream after the fermentation product is separated from the beer; allowing the transglutaminase to bind proteins in the process stream; and performing solid-liquid separation to isolate solids, including at least proteins, from the process stream to yield one or more solids streams and liquid streams including a clarified liquid stream.

In some aspects, the methods further comprise the step of producing a high protein feed product from a solids stream.

In some embodiments, the ethanologen is a yeast that produces lysine. In some embodiments, the high protein feed product is lysine rich.

In some aspects, the methods further comprise recycling a portion of the clarified liquid stream to the fermentation system.

Provided herein are methods for processing whole stillage in an ethanol plant. The methods comprise the following steps, not necessarily in the listed order: adding a transglutaminase source to a fermentation reactor or to post-fermentation stillage, separating a thin stillage liquid from the whole stillage; separating a clarified liquid stillage from the thin stillage liquid; and sending a portion of the clarified liquid stillage to a fermentation apparatus for utilization as backset.

Provided herein is a composition comprising: a stillage, whole stillage, or bottoms obtained as a by-product of fermentation and a transglutaminase source. In some aspects, the transglutaminase source is a microorganism that expresses transglutaminase. In some aspects, the transglutaminase source is in reagent form. In some aspects, the stillage is a by-product of fermentation performed using yeast which produces excess lysine.

In some embodiments, provided herein is a transglutaminase engineered to operate at a pH range between about 3.0 and about 5.0 and/or a temperature range of about 80° C. and 95° C. The transglutaminase can be expressed in *Streptoverticillium mobaraense* or *Saccharomyces cerevisiae*, for example, or any other microorganism suitable for use in the methods described herein. In some embodiments, provided herein is a vector comprising a polynucleotide encoding a transglutaminase engineered to operate at a pH range between about 3.0 and about 5.0 and/or a temperature range of about 80° C. and 95° C.

DESCRIPTION

Figure 1:
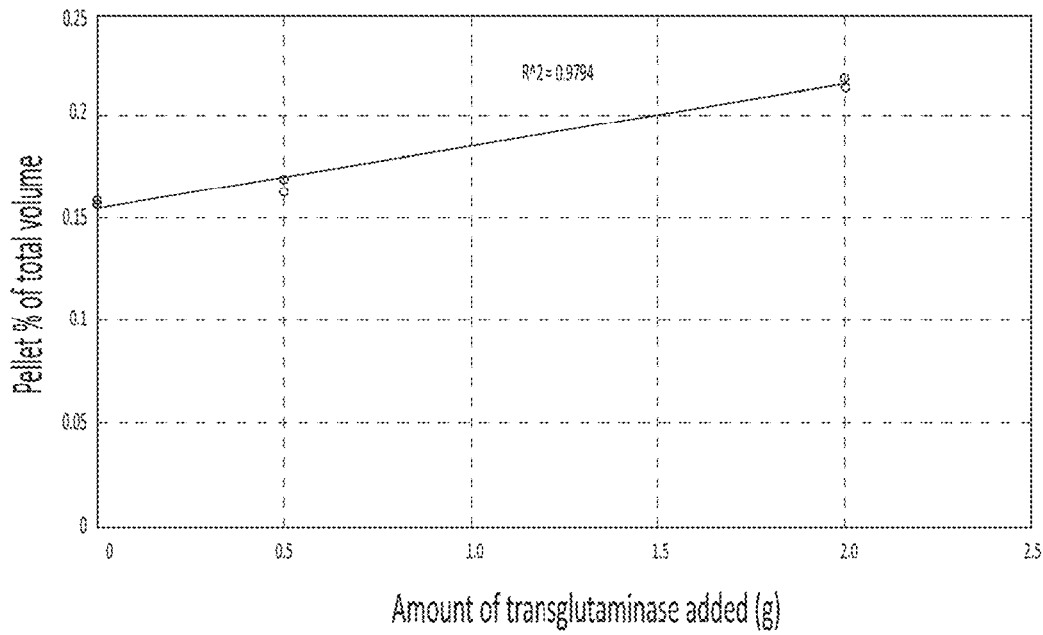
FIG. 1 shows that transglutaminase treated diluted and defatted syrup increases pellet volume relative to untreated samples, and that the increase in pellet volume is dose dependent.

Provided herein are methods, compositions, and systems involving transglutaminase. Treatment of various solid and liquid streams produced during fermentation or during post-fermentation processes with transglutaminase provides opportunities and solutions not yet considered in the biofuels industry: 1) clarified thin stillage, and 2) isolated protein for a high protein premium by-products e.g. dried distillers grains with solubles (DDGS) and grain distiller's dried yeast (GDDY—recovered yeast which is dried and is high in protein).

The inventors have identified and disclose herein the ability to biologically achieve clarified thin stillage and isolate proteins without relying solely on mechanical solutions.

In a typical ethanol production plant, corn, or other suitable feedstock is ground for fermentation. The entire corn kernel can be ground for fermentation, or the corn kernel may be fractionated into its component parts, and only the starchy endosperm ground for use in fermentation. Any suitable feedstock, subjected to virtually any suitable pretreatment, may be used in the methods provided herein.

The ground corn or other feedstock may be combined with water to form a slurry, and the pH of the slurry mixture may be adjusted as needed. A yeast such as S. cerevisiae and/or other microbial ethanologens are added to the fermenter. The amount of yeast starter employed, for example, is selected to effectively produce a commercially significant quantity of ethanol in a suitable time, e.g., less than 75 hours or less than 88 hours.

The ethanologen such as yeast can be added to the fermentation by any of a variety of methods known for adding yeast to fermentation processes. For example, yeast can be added as active dry yeast, crème yeast, or other forms. Yeast can be added directly to a fermentation vessel or it may be propagated and/or conditioned prior to adding to a fermentation vessel. In an embodiment, yeast is added as a single inoculation. In an embodiment, yeast is added to the fermentation during the fermenter fill at a rate of 5 to 100 pounds of active dry yeast (ADY) per 100,000 gallons of fermentation mash. In an embodiment, the yeast can be acclimated or conditioned by incubating about 5 to 50 pounds of ADY per 10,000 gallon volume of fermenter volume in a prefermenter or propagation tank. Incubation can be from 8 to 16 hours during the propagation stage. The prefermenter used to inoculate the main fermenter can be from 1 to 10% by volume capacity of the main fermenter, for example, from 2.5 to 5% by volume capacity relative to the main fermenter. In an embodiment, aeration is used during at least a portion of fermentation fill and/or during propagation in a prefermenter to encourage yeast growth.

Other desired nutrients can be added to the fermenter, including certain enzymes which produce monomeric sugars from polymeric sugars (e.g. glucose from starch) in the fermentable solids as in simultaneous saccharification and fermentation (SSF). These enzymes can be commercially sourced, may be present in the feedstock (genetically modified corn, for example), or may be expressed by the yeast. Exemplary enzymes include glucoamylase and alpha-amylase. Alternatively, saccharification can be performed separate from fermentation.

The slurry can be held at specified temperatures to facilitate the production of ethanol for a determined period of time. Fermenting can include contacting a mixture including sugars from the reduced feedstock (e.g., ground grain) with yeast under conditions suitable for growth of the yeast and production of ethanol. During fermentation, the yeast converts the glucose to ethanol and carbon dioxide. The rate of enzymatic production of glucose (saccharification) and the rate of the fermentation process may be established so that the level of glucose may be maintained in the system at a low steady state. After fermentation, further treatment and/or distillation is performed to recover the ethanol, oil, $CO_2$, dried distiller's grains (DDGs), and/or other co-products.

The liquid byproduct from ethanol distillation is known as stillage, whole stillage, or still bottoms. The solids content of the still bottoms can be anywhere from 5% to 16% solids content, depending on the starting solids of the prior fermentation. This stillage is typically separated using varying solids/liquids separation techniques, typically decanter centrifuges, into a liquid stream or fraction known as thin stillage and a solids fraction known as wet cake. The thin stillage contains suspended and dissolved solids that are not efficiently removed into the cake fraction by the mechanical separation technique. Total solids in the thin stillage can vary between 4% and 10% total solids, approximately equally divided between suspended and dissolved solids.

Recycling some of the thin stillage (e.g. as fermentation backset) is a way to reduce fresh water use, provide nutrients for the yeast, and maintain water balance in the system. However, recycling is limited by the amount of residual suspended and dissolved solids present in recycled streams. Removing protein solids from the thin stillage allows for more solids in the form of starch from fresh ground grain to be added for the subsequent fermentation. In addition, any protein removed from the thin stillage can be recovered as a co-product, e.g. a high protein feed product. Any thin stillage not recycled as backset is typically evaporated to produce a higher solids syrup for subsequent final drying with the wet cake fraction in a large drying apparatus. Evaporation efficiency is also limited by the amount of residual suspended solids present in the thin stillage stream.

Transglutaminases (TGase) are typically extracellular enzymes biosynthesized by microorganisms such as yeast and bacteria, including *Streptoverticillium* sp. Transglutaminases, including microbial transglutaminases (mTGase), catalyze the formation of an isopeptide bond between y-carboxamide groups of glutamine residue side chains and ε-amino groups of lysine residue side chains. More specifically, TGase catalyze acyl transfer reactions, deamidation, and crosslinking (polymerization) between protein intra- or interchain glutamine (acyl donor) and lysine (acyl acceptor) peptide residues. Transglutaminases function as transferases and are widely known to modify functional properties of proteins in food systems. A primary mode of action involves polymerization, causing changes in hydrophobicity of the proteins which results in the formation of extensively cross-linked, generally insoluble protein polymers. A temperature of 40° C. at pH 5.5 is most favorable for the catalytic activity of existing TGase enzymes.

Presently, transglutaminases are used to bond proteins together and can be used as a binding agent to improve the texture of protein-rich foods. Transglutaminases are also used in molecular gastronomy to meld new textures with existing tastes. Transglutaminases used according to the methods and systems provided herein can be commercially sourced, may be expressed by the yeast used in fermentation, or may be expressed by yeast or bacteria added to the system during or after fermentation.

Transglutaminases can be expressed in various strains of *Saccharomyces cerevisiae* such as, e.g., non-genetically modified commodity yeasts or consolidated bioprocessing yeasts (CBP, expressing glucoamylase and/or alpha-amylase). Yeast expressing transglutaminase is an economical source of the enzyme. Transglutaminase can be added to a fermentation or post-fermentation stream by adding the microorganism which expresses the enzyme, and allowing the microorganism to produce the enzyme in sufficient quantities, by adding a lysate containing the microorganism and the expressed transglutaminase, or by adding the transglutaminase as a reagent.

Historically, stillage has been separated to provide distillers' grains and oil by-products. The distiller's grains are sold as a commodity animal feed ingredient. Recently, mechanical processing of stillage has attempted to increase the value of stillage by-products by isolating smaller insolubles, but such processes have been largely inefficient. Distillers' grain can be sold wet (WDG) or dry (DDG). If thin stillage is concentrated and dried with the distillers' grain the product is dried distillers' grain with solubles (DDGS) and will have the highest protein content of traditional distillers' grains. Typical DDGS protein levels are approximately 25% by weight.

The present inventors have found that stillage may be treated with transglutaminase to more efficiently separate protein from the stillage so that, for example, stillage recycled to fermentation will have less residual protein allowing for more fresh corn solids in fermentation and more protein in the feed by products. Where transglutaminase is used to treat thin stillage after an initial solid liquid separation from whole stillage, a high protein feed can be efficiently produced that is primarily composed of yeast cells with e.g. some corn protein. When dried, this product is referred to as grain distillers' dried yeast (GDDY) and it can be used as a protein supplement, or a high protein diet for e.g. aquaculture. Protein levels from 40-60% or more can be produced.

Provided herein are methods useful in reducing and/or recovering protein levels in stillage. The methods are useful in reducing recycle water protein levels, allowing plant operators increased control over solids levels, including protein levels, in successive fermentations, either batch or continuous. The methods comprise adding transglutaminase to a fermentation or to a post-fermentation stream either directly or by adding an organism that expresses transglutaminase and separating protein bound by the transglutaminase after fermentation (e.g. from the beer or stillage) and recycling process water post-fermentation. A decrease in the protein levels in the recycled process waters can increase the amount of corn solids that can be added to the subsequent fermentation. In some aspects, the source of transglutaminase is a yeast engineered to express transglutaminase, and the methods comprise inoculating a feedstock with the engineered yeast, and fermenting the feedstock.

The methods are also useful in increasing the amount of protein in DDGS. By adding transglutaminase, or a source of transglutaminase, to a post fermentation stream, the proteins present in the stillage are cross-linked and can be captured with other solids to form wet cake (WDG) or DDGS. By capturing proteins from the stillage into the solids stream, the protein content of the solids stream can be increased by about 1% to about 5%.

The methods are also useful in formulating high protein feed products. Thin stillage, as noted above, contains between 4% and 10% total solids, some of which is suspended and some of which is dissolved. By adding transglutaminase, or a source of transglutaminase, to thin stillage, the captured proteins can be dried and used as a high protein feed product or protein supplement. An exemplary feed product is the grain distillers' dried yeast, or GDDY. Feeds and supplements can be prepared for livestock, pets, fish, and insects.

By functioning as a crosslinking enzyme, transglutaminase can increase the particle size of the suspended proteins remaining in the liquid fraction, enhancing the efficiency of any solids/liquid separation step. Increased particle size can enhance centrifugation efficiency as particle size is the most important factor determining the separation efficiency of precipitates from a suspended fluid during gravity settling or centrifugation as described by Stokes' law, which describes settling for a single compact sphere in an expanse of fluid.

Provided herein are methods of extracting or recovering protein from post fermentation process streams such as beer, stillage, or thin stillage. The methods comprise adding transglutaminase to fermentation, beer, stillage, or thin stillage. The transglutaminase is added and incubated for up to about 24 hours, for example, for about 30 minutes to about 12 hours, or about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, or about 24 hours. Incubation times depend on the concentration and activity of the transglutaminase added to the process stream, and on the form of transglutaminase, i.e. reagent, lysate (of transglutaminase expressing microorganism), or transglutaminase expressing microorganism. For example, if added as a reagent, or added as lysate, the incubation times can be shorter. If added to beer, it can take up to 24 hours for complete flocculation, particularly if the transglutaminase source is a microorganism expressing the enzyme.

After incubation, the flocculated protein is isolated from the stillage, and the de-proteinated stillage can be recycled through the fermenter as a portion of the water needed to form the slurry. The isolating can be achieved by centrifugation, filtering, settling, dissolved air flotation, or any solid/liquid separation technique. The flocculated protein can then be used to generate a high protein feed product, including DDGS or GDDY.

Transglutaminases enhance the efficiency of any solids/liquid protein separation step, as well as provide a specific technique for enhancing the recovering of essential amino acids like lysine from fermentation substrates like corn, or any other feedstock that is typically low in lysine. Typically, not all lysine ends up in DDGS. Furthermore, lysine is the most reactive amino acid, and susceptible to degradation, e.g. by Maillard reactions. Transglutaminase in stillage or thin stillage crosslinks lysine and glutamine such that it captures available lysine and bioprotects the lysine from adverse Maillard reactions, preventing formation of a degradation by-product lacking nutritional value.

In some aspects, the transglutaminase forms a protein gel. The methods herein can further comprise a step comprising providing a protease to hydrolyze the gel to release the water in the gel to facilitate drying of the protein. This step can be subsequent to separation of the flocculated proteins from the clarified liquid stream.

Fermentation yeast can be engineered to increase or augment the essential amino acid content of low essential amino acid feedstocks during the ethanolic fermentation, much like a CBP yeast can be utilized to express enzymes during the ethanol fermentation. A yeast over-expressing lysine, for example, during the ethanolic fermentation is an illustrative example. These yeast comprise a major portion of the thin stillage suspended solids fraction. If not recovered, the yeast remains in the stillage fraction and may eventually be incorporated into the DDGS coproduct to boost DDGS lysine levels. If separately recovered, the yeast produces a higher value protein rich fraction with an enhanced lysine content. The amino acid glutamine, which transglutaminase acts on, is also a major amino acid in yeast cells. A lysine producing yeast provides enhanced cross linking effects when combined with the methods of using transglutaminase described herein.

TABLE 1

Amino Acid Content of Yeast

|  | Ammonium | Glutamic acid | Amino acids |
|---|---|---|---|
| Alanine | 87.4 | 60.0 ± 1.0 | 74.0 ± 3.6 |
| Arginine | 60.3 | 58.7 ± 0.5 | 94.9 ± 4.3 |
| Asparagine-Aspartic acid | 98.6 | 95.9 ± 1.3 | 97.0 ± 2.4 |
| Cysteine | 13.1 | 12.7 ± 0.3 | 10.8 ± 0.5 |
| Glutamine-Glutamic acid | 144.7 | 216.2 ± 0.1 | 116.8 ± 3.1 |
| Glycine | 47.8 | 47.9 ± 0.1 | 46.1 ± 2.0 |
| Histidine | 22.4 | 22.1 ± 0.8 | 22.5 ± 0.6 |
| Isoleucine | 49.3 | 48.8 ± 0.2 | 47.5 ± 2.0 |
| Leucine | 71.8 | 73.1 ± 0.1 | 69.6 ± 2.0 |
| Lysine | 79.9 | 78.0 ± 0.6 | 76.4 ± 3.0 |
| Methionine | 16.7 | 16.5 ± 0.1 | 15.8 ± 1.2 |
| Phenylalanine | 40.3 | 41.3 ± 0.2 | 38.5 ± 1.8 |
| Proline | 35.1 | 38.6 ± 0.7 | 33.5 ± 1.2 |
| Serine | 52.0 | 55.8 ± 0.8 | 50.6 ± 2.4 |
| Threonine | 48.7 | 50.6 ± 0.8 | 48.5 ± 1.7 |
| Tryptophan | 14.3[b] | 14.3[b] | 14.3[b] |
| Tyrosine | 33.9 | 36.0 ± 0.7 | 32.9 ± 0.9 |
| Valine | 60.3 | 59.5 ± 0.3 | 59.1 ± 2.1 |

Provided herein are compositions comprising transglutaminase in corn starch and/or grain fermentations. The desired amount of transglutaminase is any amount useful in flocculating protein present in the fermentation. The transglutaminase can be added in reagent form or can be expressed by an organism added to the fermentation or a post fermentation stream.

Provided herein are compositions comprising transglutaminase in post-fermentation stillage. The desired amount of transglutaminase is any amount useful in flocculating protein present in the stillage. The transglutaminase can be added in reagent form or can be expressed by an organism added to the fermentation or a post fermentation stream.

The organism can be a yeast or bacteria, genetically modified or non-GMO. An exemplary GMO useful in the methods and compositions described herein is one engineered to produce transglutaminase. In some aspects, the microorganism naturally produces transglutaminase.

Further provided herein are systems in which the methods and/or compositions disclosed herein are useful. In some aspects, a fermenter or propagator contains a composition as described above, e.g. a feedstock, transglutaminase, a microorganism, and water. The fermenter or propagator can further contain at least one other enzyme, at least one priming agent, and/or a pH adjusting agent.

Further provided are systems for ethanol production comprising one or more fermenters containing the compositions described herein. In some aspects, the system further comprises at least one of the following: a milling system for preparation of feedstock; a fermentation system; a distillation system; a solid-liquid separation system; and a process water recycle system.

For example, a milling system may grind grain that is combined with water to form a slurry that is provided to a fermentation system where it is fermented into a beer that is then distilled to isolate alcohol from stillage. Transglutaminase may be added to an aqueous process stream such as the slurry, the fermentation broth, the beer; or the stillage to bind proteins so that they flocculate for easier separation from the aqueous process stream. The solid-liquid separation system may be used to isolate solids, including proteins, from a process stream to yield one or more solids streams and liquid streams including a clarified liquid stream. A portion of the clarified liquid stream may be recycled to the fermentation system to provide a portion of the water needed to form the slurry and/or fill the fermenter.

EXAMPLES

The following examples are provided for illustrative purposes only and are not intended to limit the scope of the invention.

Example 1

POET's BPX™ fermentation process is a simultaneous saccharification and fermentation (SSF) process in which starch-based feedstocks such as corn are used for the production of ethanol. In this process, raw starch hydrolyzing enzymes break down the starch into monomeric glucose, which is then metabolized by the microorganism (e.g. yeast, *Saccharomyces cerevisiae*) to produce ethanol. This process may also be termed as raw starch hydrolysis or no cook process.

In this experiment, a lab scale BPX fermentation will be performed. Corn will be ground using a hammer mill and mixed with water to form a slurry. The slurry will be prepared by weighing out the appropriate amount of corn and water into each individual reactor. A raw starch hydrolyzing enzyme blend will be added and then the appropriate amount of yeast will be added to the reactors, mixed well, and the reactors placed in a circulating water bath.

Transglutaminase will be added to the reactor. Stillage will be obtained from the fermentation, and flocculated protein isolated from the stillage. De-proteinated stillage will be assessed for amounts of any remaining protein. The data will show an overall decrease in protein present in stillage by using transglutaminase.

Example 2

Liquid byproduct, including stillage, whole stillage, or bottoms, is obtained from ethanol distillation. Transglutaminase, having an optimum pH range of ~3.6 to 5.0 and an optimum temperature range of 80 to 95° C., is added to the liquid by-product and incubated for up to about 12 hours. After incubation, the flocculated protein is isolated from the stillage, and the de-proteinated stillage can be recycled through the fermenter as a portion of the water needed to form the slurry.

Example 3

Stillage, whole stillage, or bottoms is obtained as a liquid by-product of ethanol fermentation with a yeast which produces excess lysine. A microorganism expressing transglutaminase, the transglutaminase having an optimum activity pH range of ~3.6 to 5.0 and an optimum activity temperature range of 80 to 95° C., is added to the liquid byproduct and incubated for 24 hours. After incubation, the solids including the yeast and flocculated protein are isolated from the stillage, and the de-proteinated stillage is recycled through the fermenter as a portion of the water needed to form the slurry. The recovered solids produce a higher value protein rich fraction with an enhanced lysine content.

Example 4

Diluted, defatted syrup (similar to defatted thin stillage) is a liquid by-product of ethanol fermentation. In this example, the syrup was diluted to about 25% water, 75% syrup and brought to a pH of 5.5. 30-35 mL of syrup was added to six 50 mL centrifuge tubes along with 0 g, 0.5 g, and 2 g of transglutaminase, and shaken.

Figure 2:
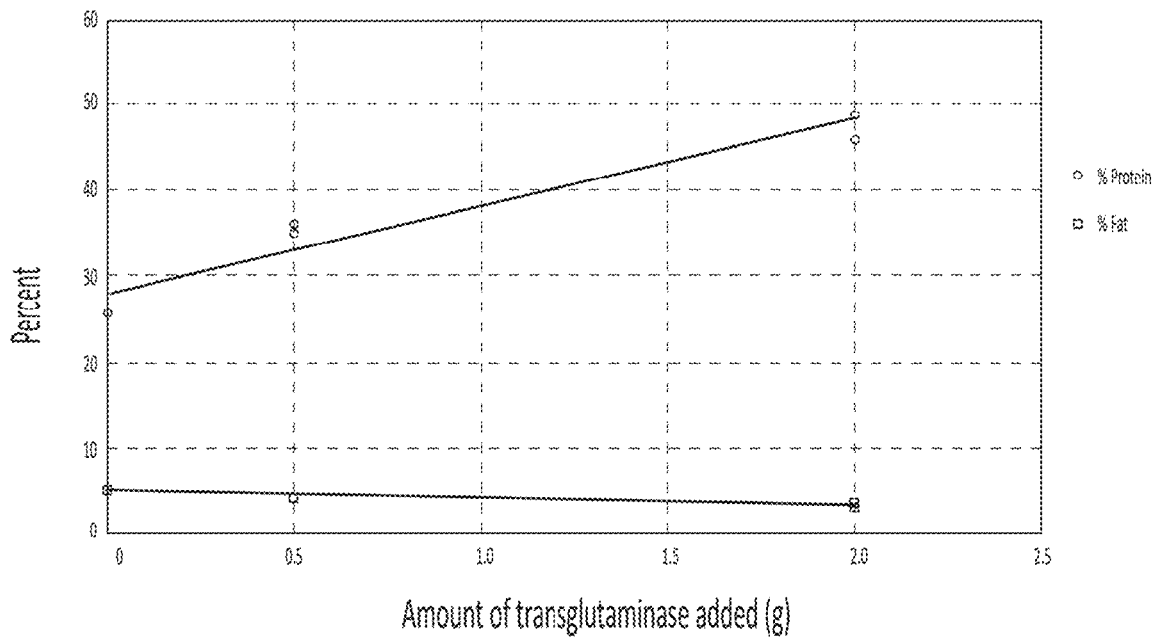
FIG. 2 shows that transglutaminase treated diluted and defatted syrup increases protein content in the pellet relative to untreated samples, and that the increase in protein content is dose dependent.

The mixture was incubated in a water bath at 40° C. for 60 min, shaking the tubes every 20-30 minutes. After the 60 minute incubation, the tubes were shaken, and the pH of the mixtures measured. The tubes were centrifuged for 2 minutes at 4500 rpm. The total volume and pellet volume of each was measured. The pellets were removed and freeze dried before measuring the protein and fat composition. FIG. 1 shows the pellet volume increased with the increase in transglutaminase dose, and FIG. 2 shows the protein content of the pellet increased with the transglutaminase dose. Thus, the data indicates the transglutaminase precipitates additional proteins out of the diluted defatted syrup into the pellet, and the protein content is dose dependent.

Example 5

Figure 3:
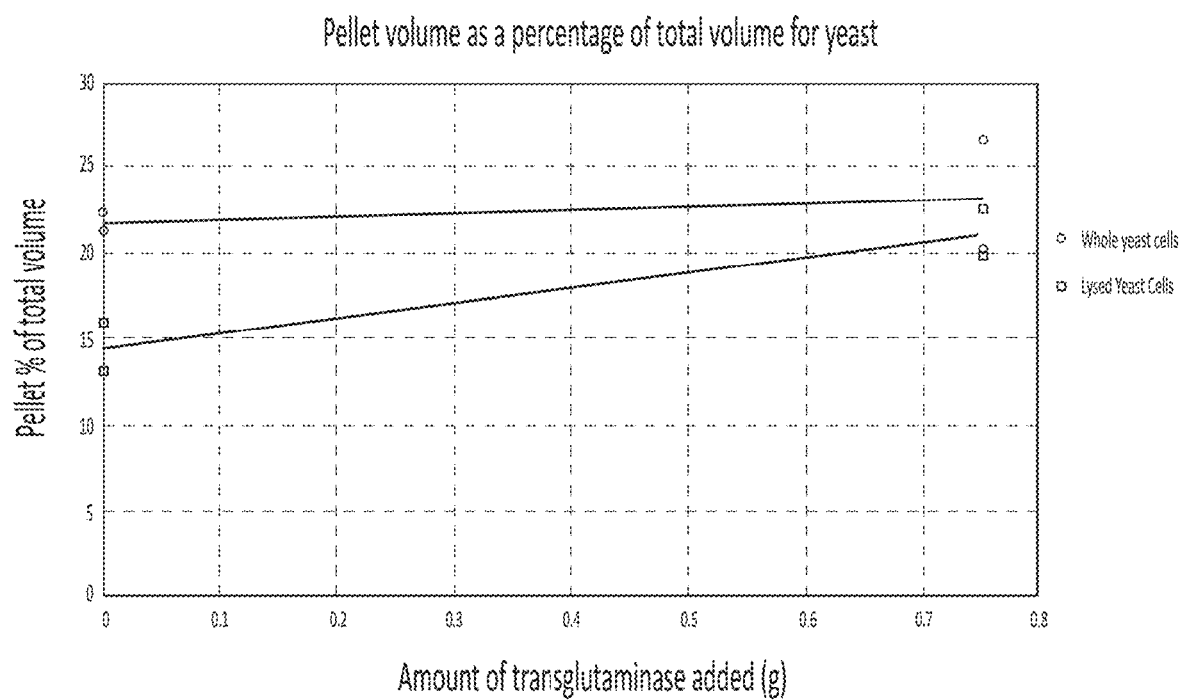
FIG. 3 shows that whole yeast cells and yeast cell lysate, when treated with glutaminase, demonstrated increased pellet size relative to untreated samples.
Figure 4:
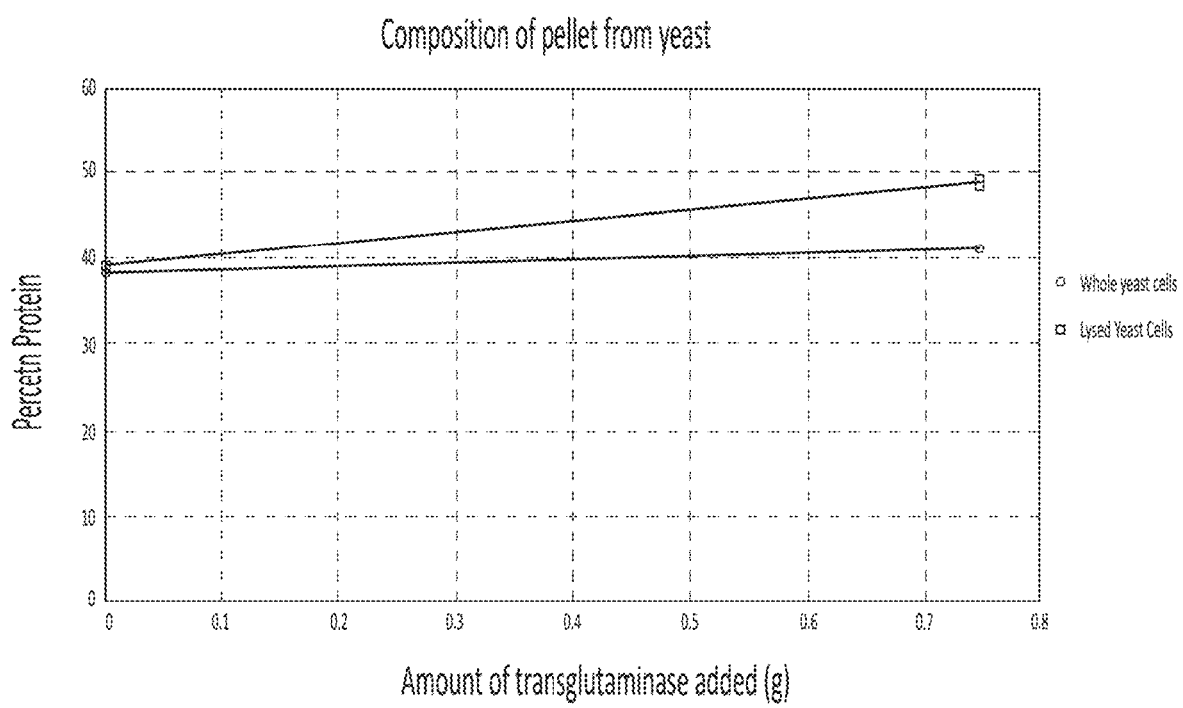
FIG. 4 shows that whole yeast cells and yeast cell lysate, when treated with glutaminase, demonstrated increased protein content in the pellet relative to untreated samples.

A mixture of 40 g Ethanol Red yeast and DI water was homogenized to form lysed yeast cells, and the amount of added water was approximated (by assuming 1 g yeast=0.5 mL). Samples with whole yeast cells were also prepared at this same concentration. Holes were placed in the test tube lids to prevent pressure build up during yeast growth. 0.75 g transglutaminase was added to each experimental test tube and the test tubes were incubated for 90 minutes at 40° C. After incubation, the test tubes were centrifuged for 2 minutes at 4500 rpm. The total volume and pellet volume of each was measured. The pellets were removed and freeze dried before measuring the protein composition. FIG. 3 shows the pellet size increased in samples treated with transglutaminase, and FIG. 4 shows the protein content of the pellet increased in samples treated with transglutaminase. This data indicates that treatment with transglutaminase can increase the protein content in DDGY.

Example 6

Whole stillage is another liquid by-product of ethanol fermentation. 130 mL of whole stillage was stirred and brought to a pH of 5.54, 30 mLs of which were placed into four 50 mL centrifuge tubes. Transglutaminase at 0.75 g was added to the treatment test tubes and the test tubes were incubated for 45 minutes at 40° C. After incubation, the test tubes were centrifuged for 2 minutes at 4500 rpm. The pellets were removed, freeze dried, and tested for protein and fat content by NMR.

Figure 5:
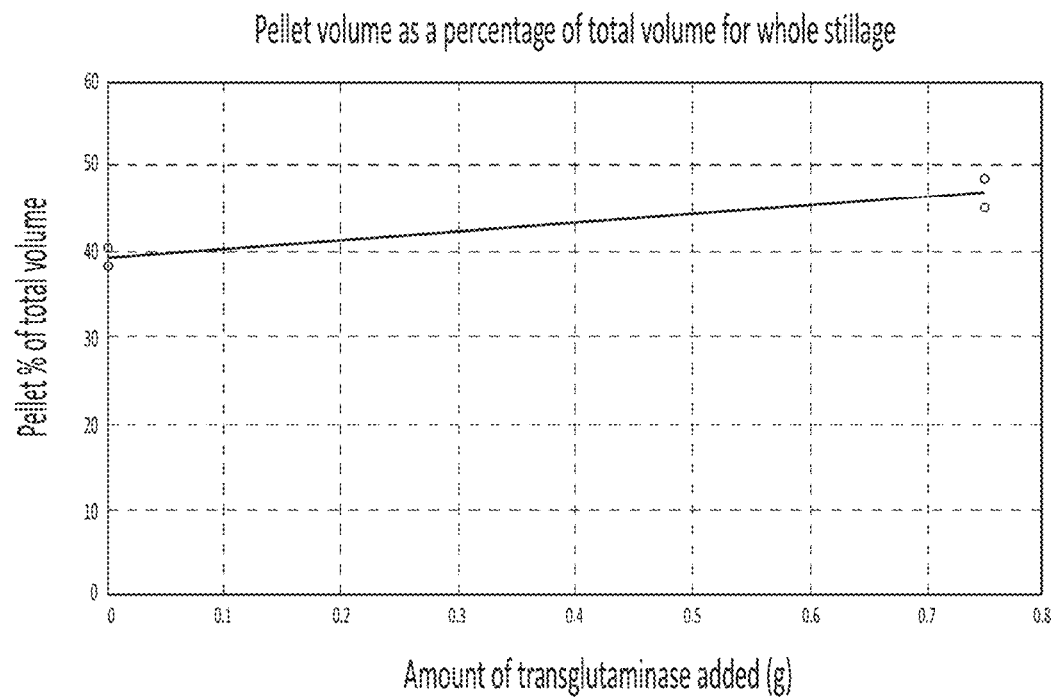
FIG. 5 shows that whole stillage treated with transglutaminase exhibits increased pellet volume relative to untreated samples.
Figure 6:
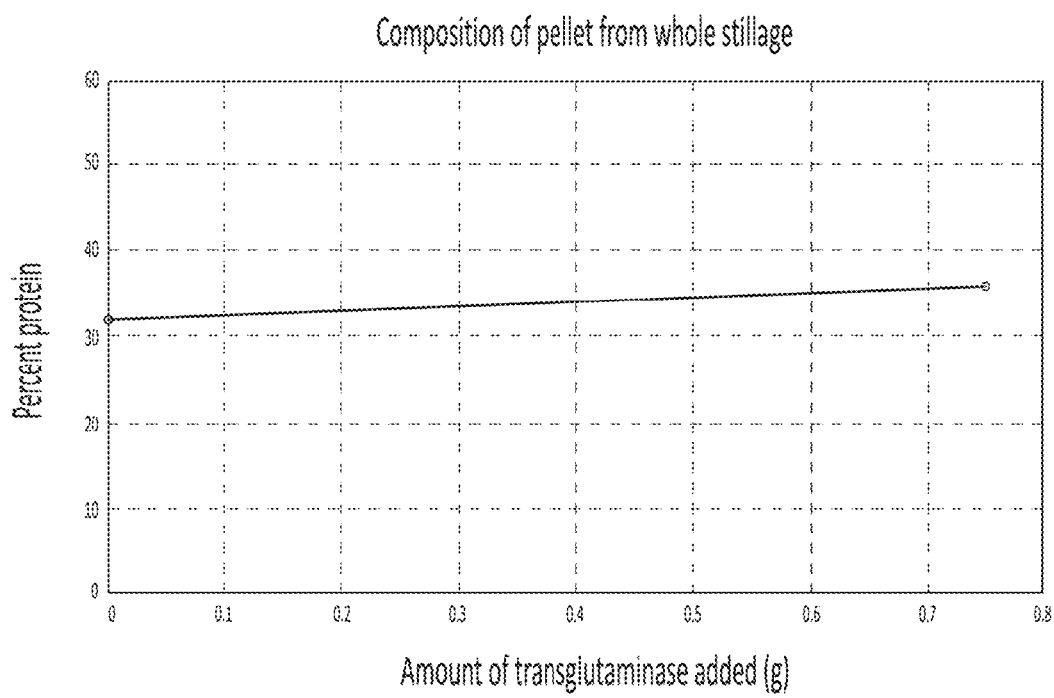
FIG. 6 shows that pellets from whole stillage treated with transglutaminase exhibits increased protein content relative to untreated samples.

FIG. 5 shows increased pellet size in the two samples treated with transglutaminase. FIG. 6 shows increased pellet protein content in the sample treated with transglutaminase. The data indicates that treatment with transglutaminase increases the amount of proteins removed from whole stillage, allowing the clarified stillage to be returned to the fermentation to make the slurry. The isolated proteins can be used to enrich livestock and fish feed products.

Example 7

Figure 7:
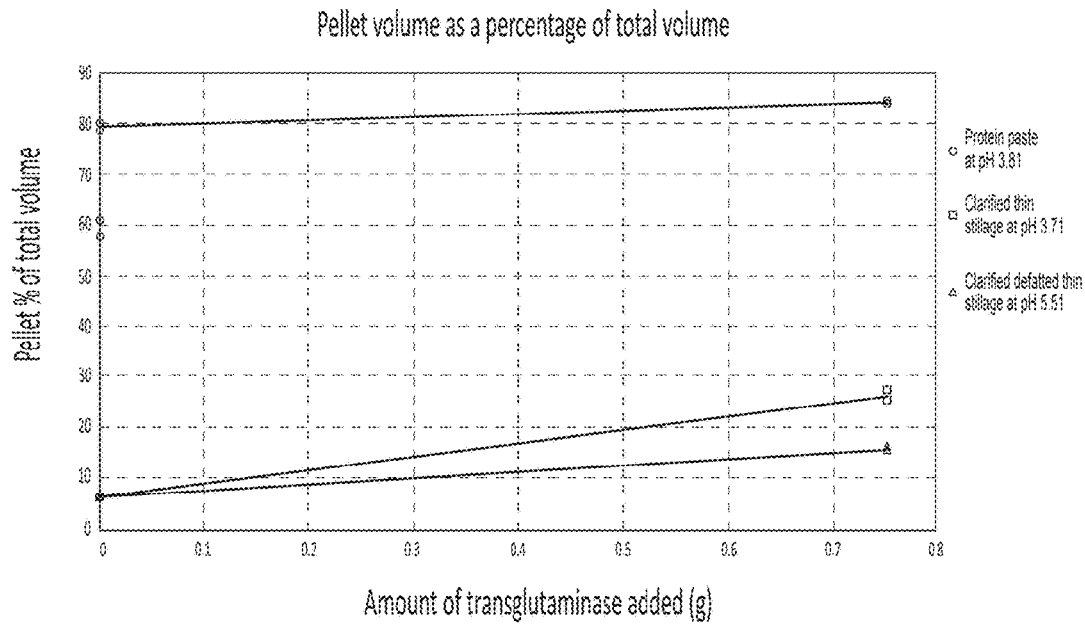
FIG. 7 demonstrates increased pellet volumes in various post-fermentation streams, including protein paste, thin stillage, and clarified defatted thin stillage, treated with transglutaminase relative to untreated samples.
Figure 8:
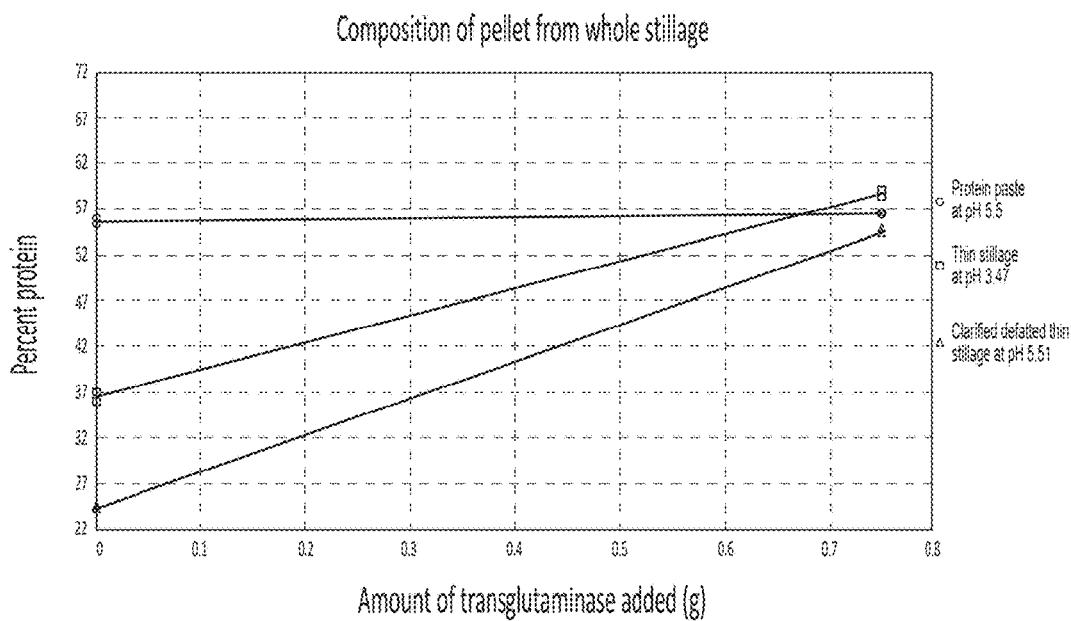
FIG. 8 demonstrates increased protein content in the pellet from various post-fermentation streams treated with transglutaminase relative to untreated samples.

In this example, various post-fermentation streams, i.e. substrates, were clarified using transglutaminase. Each substrate was placed into separate beakers and stirred, then 30 mL samples of each substrate were placed into specified 50 mL test tubes. The pH of the substrate remaining in the beakers was adjusted to 5.5, and then 30 mL samples of each pH adjusted substrate were placed in 50 mL test tubes. Transglutaminase at 0.75 g was added to the samples and the test tubes were mixed by vortexing. Incubation was carried out in a water bath incubator for 25 minutes at 40° C. The test tubes were centrifuged for 2 minutes at 4500 rpm. The supernatant was removed and the pellets were weighed, then placed into separate pre-weighed tins and freeze dried. The freeze-dried pellets were ground and then analyzed for protein and fat content. FIG. 7 shows increased pellet size in transglutaminase treated samples, and FIG. 8 shows increased protein content in transglutaminase treated samples.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A method of isolating a protein rich stream from a post-fermentation stream in an ethanol plant, the method comprising (i) separating ethanol from beer to form a first stream containing the ethanol and a second stream, (ii) adding transglutaminase to the second stream or a stream derived from the second stream whereby transglutaminase binds proteins in the second stream or the stream derived from the second stream, and (iii) isolating solids including transglutaminase bound proteins from the second stream or a stream derived from the second stream to form the protein rich stream.

2. A method of isolating a protein rich stream from a post-fermentation stream in an ethanol plant, the method comprising:
    grinding grain to provide ground grain;
    combining the ground grain with water to form a slurry;
    providing the slurry to a fermenter;
    inoculating the slurry with an ethanologen,
    filling the fermenter to provide a fermentation broth;
    fermenting the slurry to form a beer containing ethanol;
    separating the ethanol from the beer to form a first stream containing the ethanol and a second stream;
    adding transglutaminase to the second stream or a stream derived from the second stream;
    allowing the transglutaminase to bind proteins in the second stream or a stream derived from the second stream to form a bound protein stream;
    performing solid-liquid separation to isolate solids, including at least bound proteins, from the bound protein stream to yield the protein rich stream and a clarified liquid stream.

3. The method of claim 2, wherein the ethanologen is a yeast that produces lysine.

4. The method of claim 1, wherein the second stream is whole stillage, the method further comprising:
    separating the whole stillage into thin stillage and wet cake;
    adding transglutaminase to the whole stillage or thin stillage;
    separating a clarified liquid stream from the thin stillage; and
    sending a portion of the clarified liquid stream to a fermentation apparatus for utilization as backset.

5. The method of claim 1, wherein the transglutaminase is added in the form of a microorganism that expresses transglutaminase.

6. The method of claim 1, wherein the transglutaminase is added in reagent form.

7. The method of claim 2, wherein the step of fermenting is performed using yeast which produces excess lysine.

8. The method of claim 5, wherein the microorganism that expresses transglutaminase comprises a polynucleotide encoding a transglutaminase which functions at a pH range between about 3.0 and about 5.0 and/or a temperature range of about 80° C. and 95° C.

9. The method of claim 5, wherein the microorganism that expresses transglutaminase comprises a vector that comprises a polynucleotide encoding the transglutaminase.

10. The method of claim 5, wherein the microorganism is selected from the group consisting of *Streptoverticillium mobaraense* and *Saccharomyces cerevisiae*.

11. The method of claim 2, wherein the second stream or a stream derived from the second stream is exposed to transglutaminase in reagent form or an organism that expresses transglutaminase.

12. The method of claim 11, wherein the microorganism is selected from the group consisting of *Streptoverticillium mobaraense* and *Saccharomyces cerevisiae*.

13. The method of claim 1 further comprising producing a high protein feed product using the protein rich stream.

14. The method of claim 1, wherein the solids content of the protein rich stream is increased and the protein content of the protein rich stream is increased over a protein rich stream obtained from an untreated post-fermentation processing stream.

15. The method of claim 1, wherein the protein content of the protein rich stream is at least 38% protein on a dry weight basis.

16. The method of claim 5, wherein the microorganism is lysed prior to adding.

17. A method of isolating a protein rich stream from a post-fermentation stream in an ethanol plant, the method comprising:
grinding grain to provide ground grain;
combining the ground grain with water to form a slurry;
providing the slurry to a fermenter;
inoculating the slurry with an ethanologen,
filling the fermenter to provide a fermentation broth;
fermenting the slurry to form a beer containing ethanol;
separating the ethanol from the beer to form a first stream containing the ethanol and a second stream;
adding transglutaminase to the second stream or a stream derived from the second stream;
allowing the transglutaminase to bind proteins in the second stream or the stream derived from the second stream to form a bound protein stream;
performing solid-liquid separation to isolate solids, including at least bound proteins, from the bound protein stream to yield the protein rich stream and a clarified liquid stream, and
producing a high protein feed product from the protein rich stream.

18. The method of claim 17, wherein the high protein feed product is lysine rich.

19. The method of claim 17, wherein ethanol is separated from the beer via distillation.

20. The method of claim 2, wherein ethanol is separated from the beer via distillation.

21. A method of isolating a protein rich stream from a post-fermentation stream in an ethanol plant, the method comprising:
grinding grain to provide ground grain;
combining the ground grain with water to form a slurry;
providing the slurry to a fermenter;
inoculating the slurry with an ethanologen,
filling the fermenter to provide a fermentation broth;
fermenting the slurry to form a beer containing ethanol;
separating the ethanol from the beer to form a first stream containing the ethanol and a second stream;
adding transglutaminase to the second stream or a stream derived from the second stream;
allowing the transglutaminase to bind proteins in the second stream or the stream derived from the second stream to form a bound protein stream;
performing solid-liquid separation to isolate solids, including at least bound proteins, from the bound protein stream to yield the protein rich stream and a clarified liquid stream, and
recycling a portion of the clarified liquid stream as water to form a new slurry.

22. The method of claim 21, wherein ethanol is separated from the beer via distillation.

23. The method of claim 21, wherein the transglutaminase is added in the form of a microorganism that expresses transglutaminase.

24. The method of claim 21, wherein the transglutaminase is added in reagent form.

* * * * *